United States Patent
König et al.

[11] Patent Number: 5,917,083
[45] Date of Patent: Jun. 29, 1999

[54] PROCESS FOR THE MANUFACTURE OF ALLOPHANATES HAVING ISOCYANATE GROUPS

[75] Inventors: Klaus König, Odenthal; Helmut Reiff, Leverkusen; Christian Wamprecht, Neuss; Harro Träubel, Leverkusen, all of Germany

[73] Assignee: Bayer Aktiengesellschaft, Leverkusen, Germany

[21] Appl. No.: 08/907,670

[22] Filed: Aug. 8, 1997

[30] Foreign Application Priority Data

Aug. 19, 1996 [DE] Germany .................. 196 32 951

[51] Int. Cl.⁶ ..................................... C07C 269/00
[52] U.S. Cl. .................. 560/157; 560/159; 560/330; 560/158
[58] Field of Search ................... 560/157, 158, 560/159, 330

[56] References Cited

U.S. PATENT DOCUMENTS 3,730,953  5/1973  Naito et al. ............ 260/77.5 AM
4,160,087  7/1979  Yamada et al. ............ 544/28

Primary Examiner—Yogendra N. Gupta
Attorney, Agent, or Firm—Joseph C. Gil; Thomas W. Roy; Diderico van Eyl

[57] ABSTRACT

The present invention relates to a process for preparing an isocyanate group-containing allophanate corresponding to formula (I)

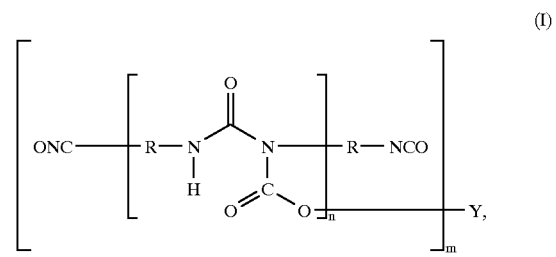

wherein

R represents the residue obtained by removing the isocyanate groups from a (cyclo)aliphatic or araliphatic diisocyanate, Y represents the represents an m-valent residue obtained by removing the hydroxyl groups from a (poly) hydroxyl compound having m OH groups and n and m are the same or different and have a value of 1 to 5, by reacting an isocyanate group-containing oxadiazinetrione with a primary alcohol in the presence of a basic catalyst having a pKa value of >6.

16 Claims, No Drawings

PROCESS FOR THE MANUFACTURE OF ALLOPHANATES HAVING ISOCYANATE GROUPS

BACKGROUND OF THE INVENTION

1. Field of the Invention

The present invention relates to a new process for the manufacture of aliphatic and/or cycloaliphatic and/or araliphatic allophanates having isocyanate groups.

2. Description of the Prior Art

Polyisocyanates containing allophanate groups are known. According to GB-A 994,890, they may be obtained by reacting isocyanates having urethane groups with excess quantities of diisocyanates, either thermally or in the presence of known catalysts such as metal chelates, metal carboxylates or tertiary amines.

A disadvantage of the (cyclo)aliphatic polyisocyanates, in particular, is that the thermal process requires very long reaction time at approx. 130–135° C., which causes yellowing, or the catalytic process results in the formation of considerable impurities, such as unreacted urethanes, isocyanurates and uretdiones having isocyanate groups.

A process is also known for the manufacture of (cyclo) aliphatic allophanates having isocyanate groups (e.g., DE-A 2,729,990) by reacting excess quantities of (cyclo)aliphatic polyisocyanates with (cyclo)aliphatic isocyanates having urethane groups in the presence of strong acids which form a mixed carbamic anhydride with (cyclo)aliphatic isocyanates.

A disadvantage of this process is the content of residual monomer in the product and the acid catalyst. The catalyst has to be removed with propylene oxide, for example, which requires a time-consuming additional reaction step.

From DE-A 2,165,023 it is known that when reacting oxadiazinetriones having anate groups (formula (II), page 3) with active hydrogen compounds such as alcohols, the two terminal isocyanate groups are reacted to form an oxadiazinetrione having urethane groups in a first reaction step and then in a second, very slow step the oxadiazinetrione ring is opened to the allophanate. This second reaction step is accelerated by means of very specific tetraalkyldistannoxane catalysts.

It is an object of the present invention to overcome the disadvantages of the prior art processes.

This object may be achieved in accordance with the process of the present invention. It has surprisingly been found that it is possible to carry out the second reaction step first and almost completely dispense with the first reaction step, if, according to the invention, oxadiazinetriones having isocyanate groups are reacted in the presence of basic catalysts with primary or secondary alcohols.

SUMMARY OF THE INVENTION

The present invention relates to a process for preparing an isocyanate group-containing allophanate corresponding to formula (I)

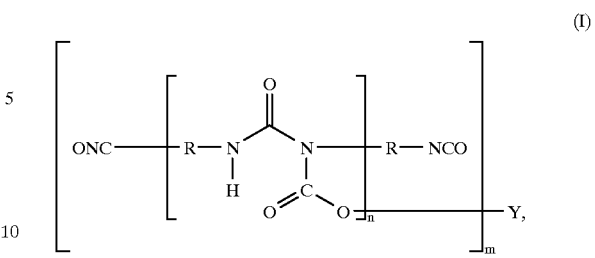

wherein
R represents the residue obtained by removing the isocyanate groups from a (cyclo)aliphatic or araliphatic diisocyanate,
Y represents the represents an m-valent residue obtained by removing the hydroxyl groups from a (poly) hydroxyl compound having m OH groups and
n and m are the same or different and have a value of 1 to 5, by reacting isocyanate group-containing oxadiazinetriones corresponding to formula (II)

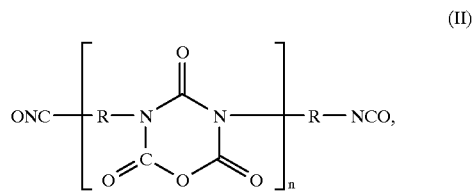

with a primary alcohol corresponding to the formula $$Y-(OH)_m$$

in the presence of a basic catalyst having a pKa value of >6.

DETAILED DESCRIPTION OF THE INVENTION

The oxadiazinetriones of formula (II) optionally contain ether, ester, carbonate, thioether or amide groups. According to the invention they are reacted with primary and/or secondary alcohols $Y(OH)_m$ having a functionality of 1 to 5, preferably 1 to 4 and a number average molecular weight range, which may be calculated from the functionality and end group analysis, of 32 to 6000 at a temperature of 0° C. to 60° C. in the presence of basic catalysts of a pKa value of >6, preferably >7.5.

In formulas (I) and (II) the R preferably represents a straight-chain aliphatic group having 4 to 12 carbon atoms, which may optionally contain ether groups and/or be substituted with methyl groups.

The alcohols used according to the invention are preferably primary aliphatic alcohols having a functionality 1 to 4 and a number average molecular weight of 32 to 6000.

The catalysts have a pKa value of >6, preferably >7.5, and are selected from tertiary, optionally cyclic, optionally heterocyclic, amines and the alkali (Na, K) and alkaline earth (Mg, Ca) salts of carbonic acid, mono, di and tricarboxylic acids, alcoholates or phenolates.

Oxadiazinetriones containing isocyanate groups are known and may be produced according to GB-A 1,145,952 from aliphatic polyisocyanates and carbon dioxide in the presence of organic compounds of trivalent phosphorus such as tributyl phosphine or trioctyl phosphine. Preferably, excess diisocyanate is used and is subsequently removed by thin layer distillation.

It is surprising that the reaction according to the invention proceeds virtually completely at temperatures of 10 to 30° C., which can easily be detected by the vigorous liberation of carbon dioxide. Generally speaking the reaction is completed after only 0.5 to 2.5 hours. According to the prior art, temperatures of 110 to 140° C. are required to convert (cyclo)aliphatic diisocyanato to allophanates.

A further advantage of the process according to the invention is that the resulting (cyclo)aliphatic diisocyanato-allophanates are produced in monomer-free form. The conventional process of thin film evaporation is may be omitted. Although the diisocyanato-oxatriazineones used as starting materials are generally present as thin-filmed resins, a substantially more favorable product/distillate ratio is obtained according to the process according to the invention, and also the occurrence of distillates contaminated with urethane groups (monomeric diisocyanates) is avoided.

A substantial advantage of the process according to the invention is that a number of polyisocyanato-allophanates can be produced from the same diisocyanato-oxadiazinetrione by varying the molecular weight and/or functionality of the hydroxyl compound.

Starting materials preparing the aliphatic and/or (cyclo) aliphatic allophanates having isocyanate groups include
A: hydroxyl and/or polyhydroxyl compounds
B: diisocyanatd-oxadiazinetriones of formula (II) and
C: basic catalysts
A: Hydroxyl and/or Polyhydroxyl compounds Both phenols (such as phenol, α-naphthol, cresol, resorcinol or trishydroxy benzenes) and aliphatic compounds having alcoholic hydroxyl groups can be used as the (poly) hydroxyl compounds having 1 to 5 OH groups, $Y(OH)_m$. The compounds having alcoholic groups are more preferred then the phenols.

Examples of the preferred alcoholic hydroxyl compounds $Y(OH)_m$ include:
1. Low-molecular mono to tetrahydric aliphatic alcohols which have a molecular weight of 32 to 250 and optionally contain ether bridges, such as methanol, ethanol, propanol, isopropanol, the isomeric butanols, pentanols, hexanols and heptanols, allyl alcohol, 2-ethylhexanol, fatty alcohols having 10 to 20 carbon atoms, ethanediol, propanediol-1,2 and -1,3, butanediol-1,2, -1,3 and -1,4, pentanediol-1,5, neopentylglycol, hexanediol-1,6 and -2,5, 3-methylpentanediol-1,5, 2-methyl-2-propylpropanediol-1,3, 2,2-diethylpropanediol-1,3, 2-ethylhexanediol-1,3, 2,2,4-trimethylpentanediol-1,3, trimethyl-hexanediol-1,6, decanediol-1,10, dodecanediol-1,12, 2-butanediol-1,4, 2-methylenepropanediol-1,3, glycerol, butanetriol, 2-hydroxymethyl-2-methylpropanediol-1,3, 1,2,6-hexanetriol, trimethylolethane, trimethylolpropane, pentaerythritol, ethylene glycol monoalkyl- or -arylether, propylene glycol-monoalkyl ether, diethylene glycol, triethylene glycol and tetraethylene glycol;
2. Cycloaliphatic mono to tetrahydric alcohols having a molecular weight of 88 to 250, such as cyclopentanol, cyclohexanol, methylcyclohexanol, trimethyl cyclohexanol, 4-tert.-butyl cyclohexanol, menthol, borneol and isoborneol, 2-hydroxydecalin, 1,2-, 1,3- and 1,4-cyclohexanediol, 2,4-dihydroxy-1,1,3,3-tetramethyl-cyclobutane, 1,4-bis-hydroxymethyl cyclohexane, bis-(4-hydroxycyclohexyl)-methane, 2,2-bis(4-hydroxycyclohexyl)-propane, 2-methyl-2,4-bis(4-hydroxycyclohexyl)-pentane, furfuryl and tetrahydro-furfuryl alcohol, bis-hydroxymethyl norbornane and dihydroxymethyl-tricyclodecane;
3. Araliphatic mono to tetrahydric alcohols having a molecular weight of 103 to 300, such as benzyl alcohol, phenylethyl alcohol, 3-phenylpropanol and 4,4'-di-(2-hydroxyethyl)-diphenylmethane.
4. Polythioethers, polyacetals, polycarbonates or particularly polyesters and/or polyethers having 1 to 4 hydroxyl groups which are known from polyurethane chemistry and have number average molecular weights, which may be calculated by end group analysis, of 250 to 8000, preferably 300 to 3000. The polyesters having hydroxyl groups include reaction products of polyhydric, preferably dihydric and optionally additionally trihydric alcohols, with polyvalent, preferably divalent, carboxylic acids.

Instead of the free polycarboxylic acids, the corresponding polycarboxylic anhydrides or corresponding polycarboxylic esters of low molecular weight alcohols or their mixtures may also be used to produce the polyesters. The polycarboxylic acids may be aliphatic, cycloaliphatic, aromatic and/or heterocyclic and may optionally be unsaturated and/or substituted, e.g., by halogen atoms. Examples of these include succinic acid, adipic acid, suberic acid, azelaic acid, sebacic acid, phthalic acid, isophthalic acid, trimellitic acid, phthalic anhydride, tetrahydrophthalic anhydride, hexahydrophthalic anhydride, tetrachlorophthalic anhydride, endomethylene tetrahydrophthalic anhydride, glutaric anhydride, maleic acid, maleic anhydride, fumaric acid, dimeric and trimeric fatty acids (such as oleic acid) optionally mixed with monomeric fatty acids, terephthalic dimethylester and terephthalic-bis-glycol ester.

Examples of polyhydric alcohols include ethylene glycol, propylene glycol-(1,2) and -(1,3), butylene glycol-(1,4) and -(2,3), hexanediol-(1,6), octanediol-(1,8), neopentyl glycol, cyclohexanedimethanol-(1,4-bis-hydroxymethylcyclohexane), 2-methyl-1,3-propanediol, glycerol, trimethylol propane, hexanetriol-(1,2,6), butanetriol-(1,2,4), trimethylol ethane, pentaerythritol, quinitol, mannitol, sorbitol, methyl glycoside, diethylene glycol, triethylene glycol, tetraethylene glycol, polyethylene glycols, dipropylene glycol, polypropylene glycols, dibutylene glycol and polybutylene glycols.

Polyesters prepared from lactones, such as ε-caprolactone or hydroxy-carboxylic acids such as ω-hydroxycaproic acid, may also be used.

The polyethers having one to four hydroxyl groups, which are also preferred according to the invention, are also known and may be produced by polymerizing epoxides such as ethylene oxide, propylene oxide, butylene oxide, tetrahydrofuran, styrene oxide or epichlorohydrin with themselves, e.g., in the presence of $BF_3$, or by the addition of these epoxides, optionally in a mixture or successively, onto starting compounds having reactive hydrogen atoms such as alcohols or phenols, e.g., water, ethylene glycol, propylene glycol-(1,3) or -(1,2), trimethylol propane and 4,4'-dihydroxydiphenyl propane.

The condensation products of thiodiglycol with itself and/or with other glycols, dicarboxylic acids or formaldehyde may be used as polythioethers. Depending on the co-components, the products are mixed polythioethers, polythioether esters or polythioether polyacetals.

Examples of polyacetals include the compounds which can be produced from glycols, such as diethylene glycol, triethylene glycol, 4,4'-dioxethqxy-diphenyldimethyl methane, hexanediol and formaldehyde. Suitable polyacetals may also be produced according to the invention by polymerization of cyclic acetals.

Suitable polycarbonates having hydroxyl groups are known and include the products obtained by the reaction of diols (such as propanediol-(1,3), butanediol-(1,4) and/or hexanediol-(1,6), diethylene glycol, triethylene glycol and tetraethylene glycol) with phosgene or diaryl carbonates such as diphenyl carbonate.

The primary aliphatic alcohols set forth under 1) and the polyester and/or polyether polyols set forth under 4) are preferably used in the process according to the invention.

Particularly preferred in the process according to the invention are long-chain primary $C_8$–$C_{36}$ fatty alcohols and polyethylene glycol-mono-$C_1$–$C_6$-alkyl ethers such as the Carbowax polyethers (polyethylene glycol monomethyl ethers having a number average molecular weight 350, 500, 750 and 1000) as well as mono to tetra alcohols containing tertiary nitrogen such as dimethylaminoethanol, N-methyldiethanol amine, triethanol amine and morpholinoethanol.

Mixtures of the above-mentioned hydroxyl compounds may not only be used, they are preferred according to the invention.

B: Oxadiazinetriones

All oxadiazinetriones are suitable for the present invention, provided that they contain two or more NCO groups in the molecule, preferably two isocyanate groups. More preferred are oxadiazinetriones corresponding to formula II) wherein R represents the residue of an aliphatic, cycloaliphatic or araliphatic diisocyanate. Examples include ethylene diisocyanate, 1,4-diisocyanatobutane, 1,6-diisocyanatohexane, trimethylhexane diisocyanate, 1,3- and 1,4-bis-isocyanatomethylcyclohexane, isophorone diisocyanate, 4,4'-diisocyanato-dicyclohexyl-methane and the ω,ω'-diisocyanates containing ether groups, e.g, those derived from diethyl ether, dipropyl ether or dibutyl ether and araliphatic diisocyanates, such as 1,3- and 1,4-xylylene diisocyanates (XDI from Messrs Takeda, Japan).

Products corresponding to formula (II) wherein n has an average value of 1 to 1.3 are preferred.

C: Catalysts

All basic compounds may be used as catalysts, provided that they have a pKa value of >6, preferably >7.5. Preferred catalysts are tertiary amines such as trimethyl amine, triethyl amine, tributyl amine, dimethylbenzyl amine, 1.4-diazabicyclo-octane, 1,5-diazabicyclo-nonene, tetramethylbutane diamine, tetramethylpropane diamine and bis-N-dimethylaminoethyl ether.

Other suitable catalysts for the process according to the invention are the alkali and alkaline earth salts of carboxylic acids such as carbonic acid, formic acid, acetic acid, propionic acid and optionally substituted benzoic acids. Phenolates such as sodium phenolate and alcoholates such as sodium methylate are also suitable catalysts.

Aromatic compounds containing nitrogen such as pyridine, mono-$C_1$–$C_4$-alkyl pyridines, dimethyl pyridines, N-dimethylamino-pyridines, diethyl pyridines and trimethyl pyridine may also be used as catalysts, provided that their pKa value is >6. Also suitable are $C_1$–$C_4$-N-alkylpyrroles, -pyrrolines, -pyrrolidines, pyrazoles, -imidazoles, -imidazolines, -imidazolidines, -1,2,3-triazoles, -1,2,4-triazoles, and also the optionally alkylated pyrimidines, pyridazines, 1,2,3-, 1,2,4-, 1,3,5-triazines, and the optionally alkylated quinolines, isoquinolines, quinoxalines and acridines.

The process according to the invention is preferably carried out without solvents. In specific cases, e.g., when using insoluble catalysts, it may be advantageous to use organic solvents such as benzene, toluene, xylene, acetone, methylethylketone, methylisobutylketone, tetrahydrofuran, N-methylpyrrolidone, dimethylacetamide, sulphone, dimethyl formamide, ethyl acetate or butyl acetate. The solvents are present in amounts such that the end products are present as 30 to 95% solutions.

In accordance with one embodiment of the process according to the invention, the oxadiazinetrione having isocyanate groups is initially introduced and a mixture of the catalyst and an approximately equivalent quantity of the hydroxy component is added dropwise at −20 to 60° C., preferably 10 to 40° C. The amount of catalyst is generally 0.25 to 2.5%. It is also possible to mix the oxadiazinetrione containing isocyanate groups with the catalyst and then introduce the hydroxyl component dropwise. The reaction is generally complete after 0.5 to 5 hours. Stirring may be continued for an additional short time at 40 to 60° C.

The end of the reaction is reached when the liberation of gas is complete. The end point of the reaction may be determined titrimetrically (NCO determination) or by IR-spectroscopy (disappearance of the ring bands).

The desired allophanates produced according to the invention are present at the end of the reaction. The catalysts are removed if required. Heterogeneous catalysts may simply be filtered off; readily volatile amines may be distilled off (under vacuum); and non-readily volatile catalysts may be neutralized or deactivated, for example, by means of equivalent quantities of acids such as phosphoric acid, hydrochloric acid, p-toluene sulphonic acid or methane sulphonic acid etc.

When implementing the process according to the invention, the nature and quantity ratios of the starting materials are preferably selected such that allophanates having at least two isocyanate groups, i.e., allophanate polyisocyanates, are obtained products. The products according to the invention are distinguished by outstanding thermal stability.

The process according to the invention may also be carried out continuously by connecting several reactors one after the other in the form of a cascade. Diisocyanato-oxatriazineone, hydroxyl compound and catalyst are continuously metered into the first reactor. By adjusting temperature and throughput it can be ensured that the reaction is complete on leaving the last reactor.

The resulting allophanate polyisocyanates may be used to produce polyurethane foams, elastomers, thermosets, coatings and adhesives.

They are particularly suitable as raw materials for high-grade, light-stable, weatherproof coatings optionally in combination with hydroxyl-functional, higher molecular weight compounds. The allophanate polyisocyanates are distinguished by their good compatibility with known polyacrylates when compared to polyisocyanates containing urethane, biuret or isocyanurate groups.

A further advantage of the process according to the invention is the possibility of varying the nature and amounts of the compounds having hydroxyl groups. The NCO functionality of the products according to the invention can be controlled within wide limits depending upon the choice of the hydroxyl compound. The use of fatty alcohols produces products with good solubility in petrol. Outstanding hardness of the lacquer coats may be achieved by using cycloaliphatic or aromatic hydroxyl compounds.

The storage stability of the allophanate polyisocyanates produced according to the invention is excellent. The products exhibit no tendency to separate monomeric starting isocyanate and, thus, possess this advantage over the known polyisocyanates containing biuret groups.

The invention is further illustrated but is not intended to be limited by the following examples in which all parts and percentages are by weight unless otherwise specified.

EXAMPLES

Polyisocyanate 1: diisocyanato-oxadiazinetrione prepared from hexamethylene diisocyanate and having an NCO content of 21.0 wt. % and a viscosity of 2500 mPas (Baymicron OxaWM 06, Bayer AG).

Polyisocyanate 2: polyisocyanate 1 after purification via a molecular evaporator; the colorless polyisocyanate has an NCO content of 22.5 wt. % and a viscosity of 2100 mPas.

Polyisocyanate 3: a diisocyanato-oxadiazinetrione prepared from xylylene diisocyanate, carbon dioxide and tributyl phosphine as catalyst; the polyisocyanate is a highly-viscous, yellowish-brown resin having an NCO content of 17.3 wt. %.

Example 1

100 g (0.25 moles) of polyisocyanate 1 were introduced at 20° C. A mixture containing 15 g (0.25 moles) of n-propanol and 2.4 ml of triethyl amine was added dropwise within approx. 10 minutes and the temperature was controlled such that it did not exceed 20° C. The reaction mixture was further agitated at room temperature until no further $CO_2$ was given off (approx. 60 minutes). Stirring was continued for a further hour at 50° C. A clear product having an NCO content of 16.5 wt. % was obtained. The $CO_2$ volume measured was 4.3 liters, which corresponded to a gas yield of 80.4%. The crude product was degassed and kept for two hours at 50 to 60° C. and 20 to 25 mbars to remove the triethyl amine catalyst.

IR and NMR spectroscopy examinations showed that the end product substantially contained the corresponding allophanate diisocyanate of formula 1).

Examples 2–9

The procedure of Example 1 was repeated with the exception that the catalysts set forth in the following Table were used.

| Ex. | Alcohol | Catalyst | Quantity (g/100 g) Catalyst | Liters $CO_2$ | % NCO found |
|---|---|---|---|---|---|
| 2 | n-propanol | 1.5-diazabicyclo-undecenone | 1 | 4.8 | 16.2 |
| 3 | n-propanol | dimethylbenzyl amine | 1 | 2.7 | 14.1 |
| 4 | n-propanol | potassium carbonate (1) | 5 | 4.9 | 14.4 |
| 5 | n-propanol | potassium acetate (1) | 5 | 4.5 | 15.9 |
| 6 | n-propanol | triethyl amine | 1 | 4.5 | 16.3 |
| 7 | n-propanol | triethyl amine | 2 | 4.3 | 16.5 |
| 8 | n-propanol | triethylene diamine | 1 | 5.0 | 16.6 |
| 9 | methanol | sodium methylate (1) | 0.3 | 4.2 | 16.3 |

(1) 75% in dimethyl acetamide

Examples 10 to 21

The procedure of Example 1 was repeated with the exception that 0.25 moles of the alcohols set forth in the following Table were used. 1 g of triethyl amine per 100 g of reaction mixture was used as catalyst in each example.

| Ex. | Alcohol | Wt. % NCO calculated | found |
|---|---|---|---|
| 10 | Glycerol ketal | 17.2 | 15.9 |
| 11 | Methoxypolyethyleneglycol, MW 350 | 11.9 | 10.5 |
| 12 | Methoxypolyethyleneglycol, MW 500 | 10.4 | 9.2 |
| 13 | Methoxypolyethyleneglycol, MW 750 | 7.6 | 7.2 |
| 14 | Polyether LB (2) | 3.2 | 3.2 |
| 15 | Morpholinoethanol | 17.2 | 15.5 |
| 16 | N,N-dimethylaminoethanol | 18.9 | 16.2 |
| 17 | N-methyldiethanol amine | 17.7 | 16.0 |
| 18 | n-nonanol | 16.8 | 13.5 |
| 19 | Isopropanol (3) | 20.1 | 17.8 |
| 20 | 2.5-hexanediol (3) | 17.7 | 13.7 |
| 21 | Olein alcohol | 13.5 | 13.1 |

(2) n-butanol-started polyoxyethylene-polyoxypropylene-polyether of molecular weight 2250
(3) substantially lower gas yield

Examples 22–25

The procedure of Example 1 was repeated with the exception that 0.25 moles of the diols and/or polyhydroxyl compounds set forth in the following Table were used. 1 g of triethyl amine per 100 g of reaction mixture was used as catalyst in each example.

| Ex. | Alcohol | Wt. % NCO calculated | found |
|---|---|---|---|
| 22 | Diethylene glycol | 18.2 | 16.9 |
| 23 | 1.4-butanediol | 18.8 | 17.2 |
| 24 | Octaethylene glycol | 14.5 | 13.1 |
| 25 | Hexanediolneopentylglycol-polyadipate, MW 1700 (1) | 4.1 | 4.2 |

(1) 75% in dimethyl acetamide

Examples 26–28

The procedure of Example 1 was repeated using 11.5 g of ethanol as the alcohol, 1.3 g of triethyl amine as the catalyst and 0.25 moles of the diisocyanato-ozadiazinetriones set forth in the following Table.

| Ex. | Diisocyanato-oxadiazinetrione | Wt. % NCO calculated | found |
|---|---|---|---|
| 26 | Polyisocyanate 1 | 20.9 | 18.2 |
| 27 | Polyisocyanate 2 | 22.4 | 20.9 |
| 28 | Polyisocyanate 3* | 17.1 | 16.1 |

*75% in acetone.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing an isocyanate group-containing allophanate corresponding to formula (I)

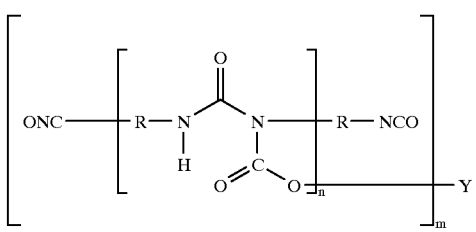 (I)

wherein
R represents the residue obtained by removing the isocyanate groups from a (cyclo)aliphatic or araliphatic diisocyanate,
Y represents an m-valent residue obtained by removing the hydroxyl groups from a (poly)hydroxyl compound having m OH groups and
n and m are the same or different and have a value of 1 to 5, which comprises reacting an isocyanate group-containing oxadiazinetrione corresponding to formula

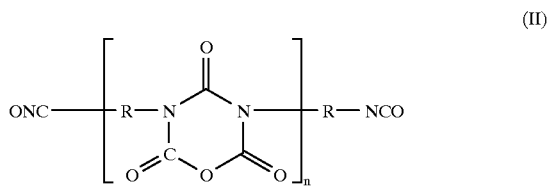 (II)

with a primary alcohol corresponding to the formula

in the presence of basic catalysts having a pKa value of >6, the catalysts comprising a component selected from the group consisting of tertiary amines, alkali earth metal salts of carboxylic acids, alkaline earth metal salts of carboxylic acids, phenolates, and alcoholates.

2. The process of claim 1 wherein R represents a straight-chain aliphatic group having 4 to 12 carbon atoms, which may optionally contain ether groups and/or be substituted with methyl groups.

3. The process of claim 1 wherein Y represents the residue obtained by removing the hydroxy groups from a primary alcohol which has a functionality of 1 to 4, has a number average molecular weight of 32 to 6000 and optionally contains a tertiary nitrogen atom.

4. The process of claim 2 wherein Y represents the residue obtained by removing the hydroxy groups from a primary alcohol which has a functionality of 1 to 4, has a number average molecular weight of 32 to 6000 and optionally contains a tertiary nitrogen atom.

5. The process of claim 1 wherein said catalyst comprises a tertiary amine, which may contain cyclic groups.

6. The process of claim 2 wherein said catalyst comprises a tertiary amine, which may contain cyclic groups.

7. The process of claim 3 wherein said catalyst comprises a tertiary amine, which may contain cyclic groups.

8. The process of claim 4 wherein said catalyst comprises a tertiary amine, which may contain cyclic groups.

9. The process of claim 5 wherein said catalyst has a pKa value of >7.5.

10. The process of claim 6 wherein said catalyst has a pKa value of >7.5.

11. The process of claim 7 wherein said catalyst has a pKa value of >7.5.

12. The process of claim 8 wherein said catalyst has a pKa value of >7.5.

13. The process of claim 1 wherein said catalyst comprises an alkali or alkaline earth salt of carbonic acid, a mono, di or tricarboxylic acid, an alcoholate or a phenolate.

14. The process of claim 2 wherein said catalyst comprises an alkali or alkaline earth salt of carbonic acid, a mono, di or tricarboxylic acid, an alcoholate or a phenolate.

15. The process of claim 3 wherein said catalyst comprises an alkali or alkaline earth salt of carbonic acid, a mono, di or tricarboxylic acid, an alcoholate or a phenolate.

16. The process of claim 4 wherein said catalyst comprises an alkali or alkaline earth salt of carbonic acid, a mono, di or tricarboxylic acid, an alcoholate or a phenolate.

* * * * *